United States Patent
Kyle et al.

(10) Patent No.: US 12,397,025 B2
(45) Date of Patent: Aug. 26, 2025

(54) METHOD FOR FACILITATING MATURATION OF THE MAMMALIAN IMMUNE SYSTEM

(71) Applicant: INFINANT HEALTH, INC, Davis, CA (US)

(72) Inventors: David Kyle, Davis, CA (US); Steven Frese, Oakland, CA (US); Samara Freeman-Sharkey, Davis, CA (US); Bethany Henrick, Davis, CA (US)

(73) Assignee: INFINANT HEALTH, INC, Davis, CA (US)

( * ) Notice: Subject to any disclaimer, the term of this patent is extended or adjusted under 35 U.S.C. 154(b) by 325 days.

(21) Appl. No.: 17/655,825

(22) Filed: Mar. 22, 2022

(65) Prior Publication Data
US 2022/0313759 A1 Oct. 6, 2022

Related U.S. Application Data

(63) Continuation of application No. 16/314,580, filed as application No. PCT/US2017/040530 on Jun. 30, 2017, now Pat. No. 11,318,175.

(60) Provisional application No. 62/397,788, filed on Sep. 21, 2016, provisional application No. 62/357,820, filed on Jul. 1, 2016.

(51) Int. Cl.
| | | |
|---|---|---|
| *A61K 35/747* | (2015.01) | |
| *A23K 10/18* | (2016.01) | |
| *A23L 33/00* | (2016.01) | |
| *A23L 33/135* | (2016.01) | |
| *A61K 31/702* | (2006.01) | |
| *A61K 35/741* | (2015.01) | |
| *A61K 35/744* | (2015.01) | |
| *A61K 35/745* | (2015.01) | |
| *C12Q 1/689* | (2018.01) | |

(52) U.S. Cl.
CPC ............ *A61K 35/747* (2013.01); *A23K 10/18* (2016.05); *A23L 33/135* (2016.08); *A23L 33/40* (2016.08); *A61K 31/702* (2013.01); *A61K 35/741* (2013.01); *A61K 35/744* (2013.01); *A61K 35/745* (2013.01); *C12Q 1/689* (2013.01); *A23V 2002/00* (2013.01); *A23V 2400/529* (2023.08); *A23V 2400/533* (2023.08)

(58) Field of Classification Search
CPC ............................. A61K 31/702; A61K 35/741
See application file for complete search history.

(56) References Cited

U.S. PATENT DOCUMENTS

| | | |
|---|---|---|
| 2010/0303837 A1 | 12/2010 | Goletz et al. |
| 2011/0066700 A1 | 3/2011 | Chao |
| 2012/0172319 A1 | 7/2012 | Chow et al. |
| 2014/0037785 A1 | 2/2014 | Barboza et al. |
| 2015/0265661 A1 | 9/2015 | Newburg et al. |
| 2016/0120915 A1 | 5/2016 | Blaser et al. |

FOREIGN PATENT DOCUMENTS

| | | |
|---|---|---|
| CN | 101272701 A | 9/2008 |
| CN | 103338775 A | 10/2013 |
| CN | 103402376 A | 11/2013 |
| CN | 103763940 A | 4/2014 |
| CN | 105166914 A | 12/2015 |
| WO | 2013154725 A1 | 10/2013 |
| WO | 2014121304 A1 | 8/2014 |
| WO | 2015095241 A2 | 6/2015 |
| WO | 2016065324 A1 | 4/2016 |
| WO | 2016066763 A1 | 5/2016 |
| WO | 2016094836 A1 | 6/2016 |
| WO | 2016105513 A1 | 6/2016 |
| WO | 2016141454 A1 | 9/2016 |
| WO | 2017053544 A1 | 3/2017 |
| WO | 2017084673 A1 | 5/2017 |

OTHER PUBLICATIONS

Sandra JM ten Bruggencate "Functional role and mechanisms of sialyllactose and other sialylated milk oligosaccharides" Nutrition Reviews, vol. 72, Issue 6, Jun. 1, 2014, pp. 377-389 (Year: 2014).*
Underwood et al., "Human milk oligosaccharides in premature infants: absorption, excretion, and influence on the intestinal microbiota." Pediatric Research 78(6): 670-677 (2015).
Bekkali et al. "Infant stool form scale: development and results." J Pediatr. 154(4): 521-526.e1 (2009).
Lozupone et al. "Diversity, stability and resilience of the human gut microbiota." Nature 489(7415): 220-230 (2012).
Schwab et al. "Lactic acid bacteria fermentation of human milk oligosaccharide components, human milk oligosaccharides and galactooligosaccharides." FEMS Microbiol Lett 315: 141-148 (2011).
Stecher et al. "'Blooming' in the gut: how dysbiosis might contribute to pathogen evolution." Nat Rev Microbiol. 11(4): 277-284 (2013).
Underwood et al., "Bifidobacterium longum subspecies infantis: champion colonizer of the infant gut." Pediatr Res 77(1-2): 229-235 (2015).
Weese et al., "Evaluation of Lactobacillus pentosus WE7 for prevention of diarrhea in neonatal foals." JAVMA 226(12): 2031-2034 (2005).

(Continued)

*Primary Examiner* — Thane Underdahl
(74) *Attorney, Agent, or Firm* — NIXON PEABODY LLP; Mark J. FitzGerald; Alissa R. Young

(57) ABSTRACT

The inventions described herein relate generally to the use of compositions to increase output of acetate and lactate while reducing pH and the levels of pathogenic bacteria and inflammation in the gut of a nursing infant mammal including humans. These compositions generally comprise one or more bacterial strains selected for their growth on mammalian milk oligosaccharides, a source of mammalian milk oligosaccharides, and, optionally, nutritive components required for the growth of that infant mammal.

19 Claims, 9 Drawing Sheets

(56) References Cited

OTHER PUBLICATIONS

Yassour et al. "Natural history of the infant gut microbiome and impact of antibiotic treatment on bacterial strain diversity and stability." Science Translational Medicine 8(343): 343ra81 (2016).
MacFarlane et al., "Regulation of short-chain fatty acid production," Proceedings of the Nutrition Society, vol. 62, 2003, pp. 67-72.
Kim et al., "Gut microbiota lipopolysaccharide accelerates inflamm-aging in mice," BMC Microbiology, vol. 16, 2016, pp. 1-9.
Bezkorovainy, "Probiotics: determinants of survival and growth in the gut," Am. J. Clin. Nutr., vol. 73, 2001, pp. 399S-405S.
Morinaga Probiotics Center, "B. Infantis M-63," 2 pages, Accessed Feb. 27, 2021.
Bannister-Tyrrell et al., "Variation in hospital caesarean section rates for preterm births," Australian and New Zealand Journal of Obstetrics and Gynaecology 2015; 55: 350-356.
Underwood, Mark A., et al. "A comparison of two probiotic strains of bifidobacteria in premature infants." The Journal of pediatrics 163.6: 1585-1591 (2013).
Bin-Nun et al., "Oral probiotics prevent necrotizing enterocolitis in very low birth weight neonates." The Journal of pediatrics 147.2: 192-196 (2005).
Hoyos, "Reduced incidence of necrotizing enterocolitis associated with enteral administration of Lactobacillus acidophilus and Bifidobacterium infantis to neonates in an intensive care unit." International Journal of Infectious Diseases 3.4: 197-202 (1999).
Judge Jorge L. Alonso. "Memorandum Opinion and Order" in *Evolve Biosystems, Inc., and the Regents of the University of California*, v. *Abbott Laboratories* (Jan. 7, 2025).
Lin et al. "Oral probiotics reduce the incidence and severity of necrotizing enterocolitis in very low birth weight infants." Pediatrics 115(1): 1-4 (2005).
Interlocutory Decision in Opposition of EP Patent 3,209,308 (Jun. 6, 2025).

\* cited by examiner

METHOD FOR FACILITATING MATURATION OF THE MAMMALIAN IMMUNE SYSTEM

CROSS-REFERENCE TO RELATED APPLICATIONS

This application is a continuation application of U.S. patent application Ser. No. 16/314,580, filed Dec. 31, 2018, which is the U.S. National Phase of International Patent Application No. PCT/US17/40530, filed Jun. 30, 2017, which claims the benefit of priority to U.S. Provisional Patent Application No. 62/397,788, filed Sep. 21, 2016, and which also claims the priority to U.S. Provisional Patent Application No. 62/357,820, filed Jul. 1, 2016, the contents of each are hereby incorporated by reference in their entireties.

FIELD OF INVENTION

The inventions described herein relate generally to the use of compositions to increase output of acetate and lactate while reducing pH and the levels of pathogenic bacteria and inflammation in the gut of a nursing infant mammal including humans. These compositions generally comprise one or more bacterial strains selected for their growth on mammalian milk oligosaccharides, a source of mammalian milk oligosaccharides, and, optionally, nutritive components required for the growth of that infant mammal.

BACKGROUND

The intestinal microbiome is the community of microorganisms that live within an animal's gastrointestinal tract, the vast majority of which is found in the large intestine or colon of mammals. In a healthy human, most dietary carbohydrates that are consumed are absorbed by the body before they reach the colon. Many foods, however, contain indigestible carbohydrates (i.e. dietary fiber) that remain intact and are not absorbed during transit through the gut to the colon. The colonic microbiome is rich in bacterial species that may be able to fully or partially consume these fibers and utilize the constituent sugars for energy and metabolism creating different metabolites for potential nutritive use in the mammal. Methods for measuring dietary fiber in various foods are well known to one of ordinary skill in the art.

The non-infant mammalian microbiome is complex and contains a diverse community of species of bacteria. This complexity begins to develop after the cessation of human milk consumption as a sole source of nutrition. Conventional teaching with regards to the non-infant mammalian microbiome is that complexity provides stability, and maintaining a diversity of microorganisms in the microbiome while consuming a complex diet is thought to be the key to promoting gut health. Lozupone, Nature, Vol. 489, pp. 220-230 (2012).

SUMMARY OF INVENTION

Creating a healthy microbiome in a mammal is necessary for the health of the mammal. While it is difficult to understand the exact makeup of the microbiome at any given time in a mammal, the inventors have found observable indicators of the health (or, conversely, dysbiosis) of the infant microbiome in the stool composition, stool frequency, stool consistency, and fecal pH. The presence of certain amounts of short-chain fatty acids (SCFA) in the stool of a mammal and more specifically acetate and lactate, can be an indication of a healthy microbiome. The inventors have discovered that the increase of certain microbes under a controlled diet of oligosaccharides will result primarily in the increase of lactate and acetate; the major contributors to the observed increase in SCFA in the colon. The present invention provides for selection techniques for those certain microbes, and methods to use those microbes for the purpose of promoting and monitoring the achievement of healthy microbiomes.

This invention provides a method for creating, maintaining, or re-establishing a healthy microbiome in an infant mammal by (a) administering a bacterial composition comprising bacteria capable of and/or activated for colonization of the colon; and (b) administering a food composition comprising Mammalian Milk Oligosaccharides (MMO). The MMO typically comprises carbohydrate polymers found in mammalian milk which are not metabolized by any combination of mammalian digestive enzymes. The MMO can include one or more of fucosyllactose, lacto-N-fucopentose, lactodifucotetrose, sialyllactose, disialyllactone-N-tetrose, 2'-fucosyllactose, 3'-sialyllactoseamin, 3'-fucosyllactose, 3'-sialyl-3-fucosyllactose, 3'-sialyllactose, 6'-sialyllactosamine, 6'-sialyllactose, difucosyllactose, lacto-N-fucosylpentose I, lacto-N-fucosylpentose II, lacto-N-fucosylpentose III, lacto-N-fucosylpentose V, sialyllacto-N-tetraose, or derivatives thereof. See, e.g., U.S. Pat. Nos. 8,197,872, 8,425,930, and 9,200,091, the disclosures of which are incorporated herein by reference in their entirety.

The MMO may be provided to the mammal in the form of a food composition. The food composition can include mammalian milk, mammalian milk derived product, mammalian donor milk, an infant formula, milk replacer, or enteral nutrition product, or meal replacer for a mammal including a human. In some embodiments, the addition of the bacterial composition and the food composition that includes MMO can occur contemporaneously, e.g., within less than 2 hours of each other.

The food composition may be sufficient to sustain the growth of the mammal. The bacteria and the food composition can be administered in respective amounts sufficient to maintain a level and composition of SCFA in the feces of said mammal. The level of SCFA can be indicative of a healthy microbiome, and more specifically the preferred make-up of the distribution of SCFA includes acetate and lactate. The SCFA can include lactic, acetic, propionic, and butyric acids, and their salts. In some embodiments, the SCFA include acetate and lactate, and these can make up at least 50% of the SCFA. The method can include the steps of: (a) obtaining a fecal sample from the mammal; (b) determining the level and composition of SCFA in the sample; (c) identifying a dysbiotic state in the mammal if the level of SCFA is too low or of skewed composition; (d) treating the dysbiotic mammal by: (i) administering a bacterial composition comprising bacteria capable of and/or activated for colonization of the colon; (ii) administering a food composition comprising MMO; or (iii) both (i) and (ii) added contemporaneously. This embodiment can provide a method of enhancing and/or monitoring the health of a mammal. The bacteria and/or the food composition can be administered in respective amounts sufficient to maintain a level of SCFA in the feces of the mammal above the threshold level in step (c).

The bacteria can be a single bacterial species of *Bifidobacterium* such as *B. adolescentis, B. animalis* (e.g., *B. animalis* subsp. *animalis* or *B. animalis* subsp. *lactis*), *B.*

*bifidum, B. breve, B. catenulatum, B. longum* (e.g., *B. longum* subsp. *infantis* or *B. longum* subsp. *longum*), *B. pseudocatanulatum, B. pseudolongum*, single bacterial species of *Lactobacillus*, such as *L. acidophilus, L. antri, L. brevis, L. casei, L. coleohominis, L. crispatus, L. curvatus, L. fermentum, L. gasseri, L. johnsonii, L. mucosae, L. pentosus, L. plantarum, L. reuteri, L. rhamnosus, L. sakei, L. salivarius, L. paracasei, L. kisonensis., L. paralimentarius, L. perolens, L. apis, L. ghanensis, L. dextrinicus, L. shenzenensis, L. harbinensis*, or single bacterial species of *Pediococcus*, such as *P. parvulus, P. lolii, P. acidilactici, P. argentinicus, P. claussenii, P. pentosaceus*, or *P. stilesii*, or it can include two or more of these species. In some embodiments, at least one of the species can be capable of consuming MMO by the internalization of that intact MMO within the bacterial cell itself. In some embodiments, at least one species of the bacteria composition can include bacteria activated for colonization of the colon. The bacteria may be grown in an anaerobic culture whose sole carbon source is wholly or partially the MMO.

In some embodiments, a method of obtaining a bacterial monoculture suitable for this invention is described as a bacterial monoculture comprising a bacterium which can grow on MMO as a sole carbon source. The bacteria may grow in an anaerobic culture whose sole carbon source is the MMO. The method can include the steps of: (a) obtaining a sample containing living microorganisms from fecal material of a nursing infant mammal that is not dysbiotic; (b) inoculating a culture medium whose sole carbon source is MMO with the sample from step (a); (c) incubating the inoculated culture anaerobically; (d) recovering a pure bacterial strain from the incubated culture of step (c), and, optionally, exposing the sample from step (a) to mutagenesis prior to the inoculating step (b). The nursing infant mammal can be an infant human.

In some embodiments, the proportion of pathogenic bacteria in the microbiome of the mammal is reduced by the treatment. In some embodiments, the pathogenic bacteria are Enterobacteriaceae (e.g., one or more of *Salmonella, E. coli, Klebsiella,* or *Clostridium*). In some embodiments, the pathogenic bacteria are reduced by greater than 10%, 15%, 25%, 50%, 75%, 80%, or 85% by the treatment.

In some embodiments, a method of reducing the antibiotic resistance gene load is described. One or more genes of the antibiotic resistance gene load may be reduced by greater than 10%, 15%, 25%, 30%, 45%, 50%, 75% or 85%. In some embodiments, a method of reducing the levels of lipopolysaccharide (LPS) and/or pathogenic bacteria in the gut of a mammal are described.

In some embodiments, the frequency of bowel movements in an infant mammal can be decreased as compared to a dysbiotic mammal. In some embodiments, the stool composition of an infant mammal can be altered as compared to a dysbiotic mammal. The firmness/consistency of the stool composition of the infant mammal can be increased as compared to a dysbiotic mammal. In some embodiments, the stool can be less watery.

In the various embodiments, the mammal is a human, buffalo, camel, cat, cow, dog, goat, guinea pig, hamster, horse, pig, rabbit, sheep, monkey, mouse, or rat. The mammal can be an infant. The mammal can be a nonhuman mammal, for example, a mammal grown for human consumption. The mammal can be a companion or performance animal.

In any embodiment according to this invention, the mammal may be an infant mammal, and the infant mammal can be an infant human. In any of the embodiments described herein, the infant mammal can be a pre-term infant or a term infant, particularly an infant born by C-section, and/or a dysbiotic infant. In any of the embodiments described herein, the infant can be a dysbiotic infant that has (a) a watery stool, (b) *Clostridium difficile* levels of greater than $10^6$ cfu/g feces, greater than $10^7$ cfu/g feces, or greater than $10^8$ cfu/g feces, (c) Enterobacteriaceae at levels of greater than greater than $10^6$, greater than $10^7$, or greater than $10^8$ cfu/g feces, and/or (d) a stool pH of 5.5 or above, 6.0 or above, or 6.5 or above. The infant mammal is generally receiving MMO. In any of the embodiments described herein, the infant can be a breast-fed infant, and/or an infant whose diet is supplemented with MMO.

The MMO can be provided at a level that is sufficient to maintain SCFA in the stool. The MMO can be supplied chronically in amounts sufficient to maintain colonization of the microbe that internalizes the MMO, and/or maintain SCFA in the stool. For example, the infant mammal can be receiving MMO at a dose representing over 10%, over 15%, over 20%, over 25%, over 30%, over 35%, over 40%, over 45%, over 50%, over 55%, over 60%, over 65%, over 70%, over 75%, over 80%, over 85%, over 90%, over 95%, or up to 100% of the total dietary fiber. MMO can be administered to the infant mammal prior to, after, or contemporaneously with the administration of the bacterial composition.

DETAILED DESCRIPTION OF THE INVENTION

Figure 1:
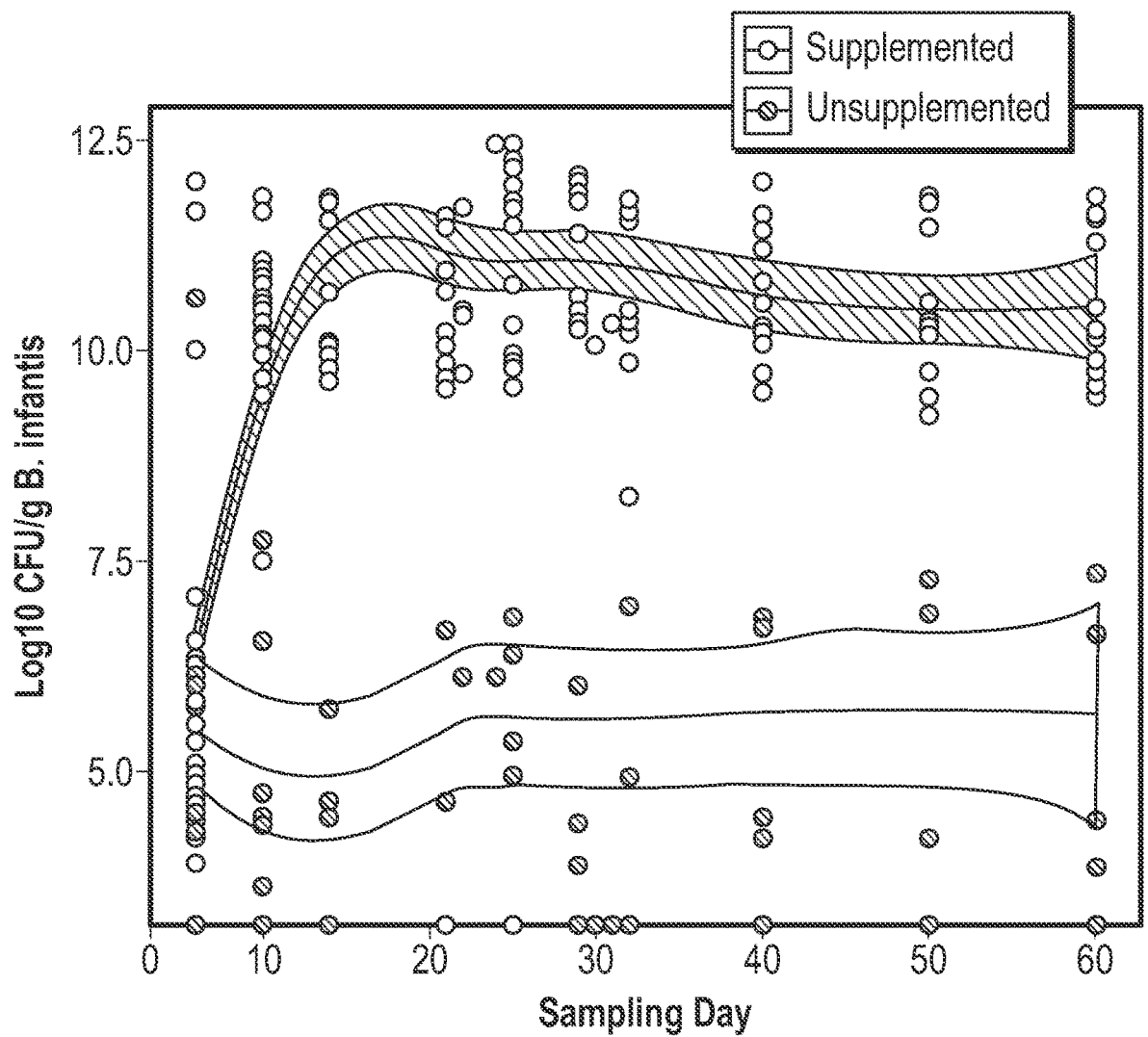
FIG. 1. Amount (CFU/g) of *B. longum* subsp. *infantis* (*B. infantis*) in fecal samples as measured by qPCR during the intervention period and a follow-up period in both vaginally- and C-section-delivered human infants. The black line and dots represent all infants who were supplemented with *B. infantis* for 21 days starting at 7 days of life. All infants receiving the standard of care (no probiotic) are depicted with the grey line and dots. The band around each line represents a 95% confidence interval around the line. The end of supplementation occurred at day 28 and samples were collected until day 60 of life.

This invention is directed to methods of monitoring, treating and preventing dysbiosis in mammalian intestines; and to compositions and devices used in the methods.

Definition of Dysbiosis

Generally, the phrase "dysbiosis" is described as the state of microbiome imbalance inside the body, resulting from an insufficient level of keystone bacteria (e.g., bifidobacteria, such as *B. longum* subsp. *infantis*) or an overabundance of harmful bacteria in the gut.

Dysbiosis in a human infant is defined herein as a microbiome that does comprises *B. longum* subsp. *infantis* below the level of $10^8$ cfu/g fecal material during the first 12 months of life, likely below the level of detectable amount (i.e., $10^6$ cfu/g fecal material). Dysbiosis can be further defined as inappropriate diversity or distribution of species abundance for the age of the human or animal. Dysbiosis in infants is driven by either the absence of MMO, absence of *B. infantis*, or the incomplete or inappropriate breakdown of MMO. For example, in an infant human, an insufficient level of keystone bacteria (e.g., bifidobacteria, such as *B. longum* subsp. *infantis*) may be at a level below which colonization of the bifidobacteria in the gut will not be significant (for example, around $10^6$ cfu/g stool or less). For non-human mammals, dysbiosis can be defined as the presence of members of the Enterobacteraceae family at greater than $10^6$, or $10^7$, or $10^8$ cfu/g feces from the subject mammal. Additionally, a dysbiotic mammal (e.g., a dysbiotic infant) can be defined herein as a mammal having a fecal pH of 6.0 or higher, a watery stool, *Clostridium difficile* levels of greater than $10^6$ cfu/g feces, greater than $10^7$ cfu/g feces, or greater than $10^8$ cfu/g feces, Enterobacteriaceae at levels of greater than $10^6$, greater than $10^7$, or greater than $10^8$ cfu/g feces, and/or a stool pH of 5.5 or above, 6.0 or above, or 6.5 or above. For example, a dysbiotic human infant can be a human infant having a fecal pH of 6.0 or higher, a watery stool, *Clostridium difficile* levels of greater than $10^6$ cfu/g feces, greater than $10^7$ cfu/g feces, or greater than $10^8$ cfu/g feces, Enterobacteriaceae at levels of greater than greater than $10^6$, greater than $10^7$, or greater than $10^8$ cfu/g feces, a stool pH of 5.5 or above, 6.0 or above, or 6.5 or above, lactate:acetate ratios of less than 2:3, and/or greater than 2.5 mmol titratable acid/g feces.

Dysbiosis in a mammal, especially an infant mammal, can be observed by the physical symptoms of the mammal (e.g., diarrhea, digestive discomfort, inflammation, etc.) and/or by observation of the presence of free sugar monomers in the feces of the mammal, an absence or reduction in specific bifidobacteria populations, and/or the overall reduction in measured SCFA; more specifically, acetate and lactate. Additionally, the infant mammal may have an increased likelihood of becoming dysbiotic based on the circumstances in the environment surrounding the mammal (e.g., an outbreak of disease in the surroundings of the mammal, formula feeding, cesarean birth, etc.). Dysbiosis in an infant mammal can further be revealed by a low level of SCFA in the feces of said mammal.

The nursing human infant's intestinal microbiome is quite different from an adult microbiome in that the adult gut microbiome generally contains a large diversity of organisms, each present at a low percentage of the total microbial population. The healthy nursing infant's microbiome, on the other hand can be made up almost exclusively (up to 80%) of a single species. When this species is B. infant's and the infant is a human infant, this dominant colonization unexpectedly gives rise to a very stable gut ecology. Microbiome stability is a desirable characteristic in the first few months of life where many developmental changes are rapidly taking place as the infant develops prior to weaning.

The transition from the simple, non-diverse microbiome of the nursing infant to a complex, diverse adult-like microbiome (i.e., weaning) correlates with the transition from a single nutrient source of a rather complex fiber (e.g., maternal milk oligosaccharides) to more complex nutrient sources that have many different types of dietary fiber.

Carbohydrates of the Infant Diet

Mammalian milk contains a significant quantity of mammalian milk oligosaccharides (MMO) as dietary fiber. For example, in human milk, the dietary fiber is about 15% of total dry mass, or about 15% of the total caloric content. These oligosaccharides comprise sugar residues in a form that is not usable directly as an energy source for the baby or an adult, or for most of the microorganisms in the gut of that baby or adult.

The term "mammalian milk oligosaccharide" or MMO, as used herein, refers to those indigestible glycans, sometimes referred to as "dietary fiber", or the carbohydrate polymers that are not hydrolyzed by the endogenous mammalian enzymes in the digestive tract (e.g., the small intestine) of the mammal. Mammalian milks contain a significant quantity of MMO that are not usable directly as an energy source for the milk-fed mammal but may be usable by many of the microorganisms in the gut of that mammal. MMOs can be found as free oligosaccharides (3 sugar units or longer, e.g., 3-20 sugar residues) or they may be conjugated to proteins or lipids. Oligosaccharides having the chemical structure of the indigestible oligosaccharides found in any mammalian milk are called "MMO" or "mammalian milk oligosaccharides" herein, whether or not they are actually sourced from mammalian milk.

The major human milk oligosaccharides ("HMO"), include lacto-N-tetraose (LNT), lacto-N-neotetraose (LNnT) and lacto-N-hexaose, which are neutral HMOs, in addition to fucosylated oligosaccharides such as 2-fucosyllactose (2FL), 3-fucosyllactose (3FL), and lacto-N-fucopentaoses I, II and III. Acidic HMOs include sialyllacto-N-tetraose, 3' and 6' sialyllactose (6SL). HMO are particularly highly enriched in fucosylated oligosaccharides (Mills et al., U.S. Pat. No. 8,197,872). Among the enzymes that produce HMO in the mammary gland is the enzyme encoded by the fucosyltransferase 2 (FUT2) gene, which catalyzes the linking of fucose residues by an α1,2-linkage to oligosaccharides found in human milk. Fucosylated oligosaccharides are known to inhibit the binding of pathogenic bacteria in the gut. HMO, and in particular the fucosylated HMO, share common structural motifs with glycans on the infant's intestinal epithelia known to be receptors for pathogens. (German et al., WO 2012/009315).

Microbes of the Healthy Newborn Microbiome

Certain microorganisms, such as *Bifidobacterium longum* subsp. *infantis* (*B. infantis*), have the unique capability to consume specific MMO, such as those found in human (HMO) or bovine (BMO) milk (see, e.g., U.S. Pat. No. 8,198,872 and U.S. patent application Ser. No. 13/809,556, the disclosures of which are incorporated herein by reference in their entirety). When *B. infantis* comes in contact with certain MMO, a number of genes are specifically induced which are responsible for the uptake and internal deconstruction of those MMO, and the individual sugar components are then catabolized to provide energy for the growth and reproduction of that microorganism (Sela et al, 2008). This form of carbon source utilization is remarkably different from most of the other colonic bacteria, which produce and excrete extracellular glycolytic enzymes that deconstruct the fiber to monomeric sugars extracellularly, and only monomers are imported via hexose and pentose transporters for catabolism and energy production. If the appropriate gut bacteria are not present (e.g., a consequence of the extensive use of antibiotics or cesarean section births), or the appropriate MMO are not present (e.g., in the case of using artificial feeds for newborns, such as infant formula or milk replacers), any free sugar monomers cleaved from the dietary fiber by extra cellular enzymes can be utilized by less desirable microbes, which may give rise to blooms of pathogenic bacteria and symptoms such as diarrhea resulting therefrom.

The inventors discovered that growing bacterial cultures under strong selective pressure of MMO as the sole nutritional source can be used as a method to select and/or identify certain bacterial species that were previously not known for their ability to grow on MMO. As a result, they have developed a process with which to produce new strains of bacteria which can be used in the present invention.

The term "bacterial monoculture", as used herein, refers to a culture of a single strain.

The bacteria for use in this invention may be selected and enriched from a population of bacteria found in a stool sample of a mammal such as, but not limited to, a human, buffalo, camel, cat, cow, dog, goat, guinea pigs, hamster, horse, pig, rabbit, sheep, monkey, mouse, or rat. The selection and enrichment can be done using a method of providing such a population with a growth medium that comprises one or more MMO as the sole carbon source and then cultivating said composition for a period of time required to allow the selective enrichment of strains of bacteria capable of growth on said MMO. All other growth conditions and media for the selection of bifidobacteria, pediococci, and/or lactobacilli use standard conditions known in the art for the cultivation of these bacteria. Following the selective enrichment of the bifidobacteria, pediococci, and/or lactobacilli species, the mixture is plated out for the purposes of isolating individual colonies that are then grown up as pure strains of bacteria capable of growth on the MMO. Pure colonies isolated from a specific mammalian species can then be grown under standard conditions for such bacteria. The population of bacteria in the stool sample or the bacteria isolated and purified from the stool sample may be treated with a chemical or physical mutagen such as, but not limited to, ethyl methyl sulfonate (EMS), X-rays, a radioactive source before selection on a growth medium comprising the MMO.

The bacteria may be in an activated state as defined by the expression of genes coding for enzymes or proteins such as, but not limited to, fucosidases, sialidases, extracellular glycan binding proteins, and/or sugar permeases. Such an activated state is produced by the cultivation of the bacteria in a medium comprising a MMO prior to harvest and the preservation and drying of said bacteria. Activation of *B. infantis* is described, for example, in PCT/US2015/057226, the disclosure of which is incorporated herein in its entirety.

The MMO used for cultivation, activation, selection, and/or storage of the bacteria of this invention can include fucosyllactose (FL) or derivatives of FL including but not limited to, lacto-N-fucopentose (LNFP) and lactodifucotetrose (LDFT), lacto-N-tetraose (LNT) and lacto-N-neotetraose (LNnT), which can be purified from mammalian milk such as, but not limited to, human milk, bovine milk, goat milk, or horse milk, sheep milk or camel milk, or produced directly by chemical synthesis. The composition can further comprise one or more bacterial strains with the ability to grow and divide using fucosyllactose or its derivatives thereof as the sole carbon source. Such bacterial strains may be naturally occurring or genetically modified and selected to grow on the fucosyllactose or its derivatives if they did not naturally grow on those oligosaccharides.

The MMO can also be sialyllactose (SL) or derivatives of SL such as, but not limited to, 3'sialyllactose (3SL), 6'sialyllactose (6SL), and disialyllacto-N-tetrose (DSLNT), which can be purified from mammalian milk such as, but not limited to, human milk, bovine milk, goat milk, or mare's milk, sheep milk or camel milk, or produced directly by chemical synthesis. The composition further comprises one or more bacterial strains with the ability to grow and divide using sialyllactose or derivatives thereof as the sole carbon source. Such bacterial strains may be naturally occurring or genetically modified and selected to grow on the sialyllactose or its derivatives if they did not naturally grow on those oligosaccharides.

The MMO can be a mixture fucosyllactose (FL) or derivatives of FL and sialyllactose (SL) or derivatives of SL which are naturally found in mammalian milk such as, but not limited to, human milk, bovine milk, goat milk, and horse milk. In preferred modes, the FL and SL or derivatives thereof may be found in a ratio from about 1:10 to 10:1.

Formulations to Treat Dysbiosis

A composition comprising (a) bacteria capable of consuming the MMO and (b) one or more MMO can be stored in a low water activity environment for later administration. The composition can further include a food, and the food can comprise the complete nutritional requirements to support life of a healthy mammal, where that mammal may be, but is not limited to, an infant. The mammal can be a human, buffalo, camel, cat, cow, dog, goat, guinea pigs, hamster, horse, pig, rabbit, sheep, monkey, mouse, or rat. The bacteria can include, but is not limited to, one or more of *B. adolescentis, B. animalis,* (e.g., *B. animalis* subsp. *animalis* or *B. animalis* subsp. *lactis*), *B. bifidum, B. breve, B. catenulatum, B. longum* (e.g., *B. longum* subsp. *infantis* or *B. longum* subsp. *longum*), *B. pseudocatanulatum, B. pseudolongum, L. acidophilus, L. antri, L. brevis, L. casei, L. coleohominis, L. crispatus, L. curvatus, L. fermenturn, L. gasseri, L. johnsonii, L. mucosae, L. pentosus, L. plantarum, L. reuteri, L. rhamnosus* (e.g. LGG), *L. sakei, L. salivarius, P. acidilactici, P. argentinicus, P. claussenii, P. pentosaceus, P. stilesii L. paracasei, L. kisonensis., L. paralimentarius, L. perolens, L. apis, L. ghanensis, L. dextrinicus, L. shenzenensis, L. harbinensis, P. parvulus,* or *P. lolii*. The composition can include at least one or more fucosidases and/or one or more sialidases produced by at least one or more bacterial strains of the composition that may be intracellular or extracellular. One preferred species can be *B. longum* subsp. *infantis*. The *B. infantis* may be activated. Activation of *B. infantis* is described in PCT/US2015/057226, the disclosure of which is incorporated herein in its entirety.

The bacteria may be present in these compositions in a dry powder form, or as a suspension in a concentrated syrup with a water activity of less than 1.0, preferably less than 0.9, more preferably less than 0.8, less than 0.7, less than 0.6 or less than 0.5, or less than 0.4, or less than 0.3 or less than 0.2 or in a suspension in an oil such as, but not limited to, medium chain triglyceride (MCT), a natural food oil, an algal oil, a fungal oil, a fish oil, a mineral oil, a silicon oil, a phospholipid, or a glycolipid. The syrup may be a concentrate of a MMO such as, but not limited to, that from human milk (HMO), bovine milk (BMO), ovine milk (OMO), equine milk (EMO), or caprine milk (CMO). The oligosaccharides can be obtained from a process that involves cheese or yogurt production and can be from whey sources such as, but not limited to, the whey permeate, or a processed whey permeate, where the processing steps may include, but are not limited to, removal of lactose, removal of minerals, removal of peptides, and removal of monosaccharides, but which in any case, results in the concentration of the MMO to levels that are greater than 20%, greater than 30%, greater than 40%, greater than 50%, greater than 60%, greater than 70%, or greater than 80% of the total dry matter of the product.

The MMO can be present in the compositions of this invention in a powder form, in the form of a concentrated syrup with a water activity of less than 1.0, optionally less than 0.9, less than 0.8, less than 0.7, or less than 0.6, or less than 0.5, or less than 0.4, or less than 0.3 or less than 0.2 or in a suspension in an oil including, but not limited to, medium chain triglyceride (MCT), a natural food oil, an algal oil, a fungal oil, a fish oil, a mineral oil, a silicon oil, a phospholipid, and a glycolipid.

The composition can also include a food source that contains all the nutritional requirements to support life of a healthy mammal. That mammal may be, but is not limited to, an infant, an adolescent, an adult, or a geriatric adult. The food source can be a nutritional formulation designed for a human, buffalo, camel, cat, cow, dog, goat, guinea pigs, hamster, horse, pig, rabbit, sheep, monkey, mouse, or rat. For example, the food source can be a food source for an infant human which further comprises a protein such as, but not limited to, a milk protein, a cereal protein, a seed protein, or a tuber protein. The food source can be mammalian milk including, but not limited to, milk from human, bovine, equine, caprine, or porcine sources. The food can also be a medical food or enteral food designed to meet the nutritional requirements for a mammal, for example, a human.

Effects of the Compositions

The inventors have discovered that providing a mammalian infant with (a) certain isolated, purified, and activated bacteria that specifically consume milk oligosaccharides and/or glycans, along with (b) MMO and glycans, either in the form of its mother's milk, or as purified MMO provided contemporaneously with the bacteria, results in the production of unexpectedly high levels of SCFA, acetic and lactic acids in particular, in the colon of that infant mammal. The inventors further found that this treatment also significantly lowered the levels of pro-inflammatory biomarkers as well as pathogenic bacteria and lipopolysaccharide (LPS). Similar observations found in humans, horses, and pigs indicate that this may be a common element among many species that provide milk as the sole source of nutrition for their infant during the first stages of life (i.e., all mammals).

Supplying the infant with these two components at this early stage can further facilitate the nominal development of the immune system and may deflect the appearance of various disease conditions seen later in life due to a maldevelopment of the immune system. The use of food compositions with these two components can also have an immediate impact on the reduction of pathogen blooms early in life, eliminating the appearance of certain symptoms such as diarrhea in certain mammals such as, but not limited to humans and horses. One or more of the MMO of a particular species, used as the sole carbon source and bacteria that demonstrate the most rapid growth on that species' MMO in culture, may be used for the purpose of colonizing the gut of that mammal.

The inventors have discovered that the above components can be added to foods other than milk, where such foods comprise all the nutritive components to sustain life of an infant mammal (e.g., artificial milks and infant formula). The inventors have also discovered that the above compositions can be preventative and/or curative to outbreaks of pathogens such as *Clostridium difficile* in in mammals such as horses if provided immediately on delivery of the infant (foaling), and the treatment further, and unexpectedly, completely eliminates the "foal heat diarrhea" that generally occurs on or about day 7-10 of the life of a horse. The inventors further discovered that, although the compositions of MMO differ from mammal to mammal, some bacteria which have the discovered characteristics, surprisingly have similar effects in mammalian species in which they are not typically found.

The gut of a mammal can be colonized with the bacteria described herein in combination with the oligosaccharides described herein. The mammal can be a human, the bacteria can be a bifidobacteria, and the MMO can be isolated from, or is chemically identical to, a HMO or a BMO. The MMO can comprise fucosyllactose (FL) or derivatives of FL and/or sialyllactose (SL) or as derivatives of SL. The bifidobacteria can be provided as *B. longum*, for example, *B. longum* subsp. *infantis*. In some embodiments, the composition is provided to the subject on a daily basis comprising from 0.1 billion to 500 billion cfu of bacteria/day. For example, the composition that is provided on a daily basis can include from 1 billion to 100 billion cfu/day or from 5 billion to 20 billion cfu/day. The composition may be provided on a daily basis for at least 2, at least 5, at least 10, at least 20, or at least 30 days. The recipient of the treatment can be a human infant.

A self-sustaining, host-specific dose of SCFA can be delivered directly to the colon by the method of this invention. Amounts of MMO to generate a ratio of about 3:2 acetate to lactate can be administered. This administration may increase the levels of SCFA including, but not limited to lactic acid, acetic acid, propionic acid, and butyric acid or salts thereof, in the colon of a mammal by at least 2-fold, at least 5-fold, at least 10-fold, at least 50-fold, or at least 100-fold as compared to a dysbiotic infant.

The levels of SCFA in the colon can be approximated by the levels of the SCFA in the feces of the mammal. The SCFA will typically include acetic acid or a salt thereof. In some embodiments, the mammal is a human, the bacteria is bifidobacteria, and the MMO is from, or is chemically identical to, a HMO or a BMO. In some embodiments, the mammal is a horse, the bacteria is bifidobacteria, and the MMO is from, or is chemically identical to, an EMO, HMO or BMO. In some embodiments, the MMO comprises fucosyllactose (FL) or derivatives of FL and/or sialyllactose (SL) or as derivatives of SL. In some embodiments, the bifidobacteria is provided as *B. longum*, or as *B. longum* subsp. *infantis*. In some embodiments, the composition is provided on a daily basis comprising from 0.1 billion to 500 billion cfu of bacteria/day. In some embodiments, the composition is provided on a daily basis comprising from 1 billion to 100 billion cfu/day and, from example, from 5 billion to 20 billion cfu/day. In a preferred embodiment, the composition is provided on a daily basis for at least 2, at least 5, at least 10, at least 20, or at least 30 days. In a most preferred embodiment, the recipient of the treatment is a human infant.

The levels of pathogenic microorganisms in the gut of a mammal can be reduced, as compared to a dysbiotic infant, significantly by treating that mammal with a daily dose of a medicament comprising a MMO and bacteria that selectively grows on that MMO. In some embodiments, the proportion of the pathogenic bacteria in the microbiome of the mammal is reduced by the treatment. In some embodiments, the pathogenic bacteria are reduced, as compared to a dysbiotic infant, by greater than 25%, 50%, 75%, 80%, or 85% by the treatment. The administration can occur for a period of from at least 2, at least 5, at least 10, at least 20, or at least 30 days. Pathogenic microorganisms include, but are not limited to: *Clostridium, Escherichia, Enterobacter, Klebsiella*, and *Salmonella* species, and their presence in the colon can be estimated by their presence in the feces of the mammal. The medicament composition comprising from 0.1 billion to 500 billion cfu of bacteria can be provided on a daily basis. A medicament composition comprising from 1 billion to 100 billion cfu, or from 5 billion to 20 billion cfu can also be provided on a daily basis. The MMO can be provided in a solid or liquid form at a dose from about 0.1-50 g/day, for example, 2-30 g/day or 3-10 g/d. The bacteria that selectively grows on the MMO can be provided contemporaneously with the MMO, or the bacteria can be provided separately to a nursing infant whose MMO are in the form of whole milk provided by nursing or otherwise.

Optimizing colon chemistry, reducing the capacity for LPS production, and/or reducing the levels of proinflammatory lipopolysaccharide (LPS) in the gut of a mammal may occur by treating that mammal with a daily dose of a medicament comprising a MMO and bacteria that selectively grows on that MMO, for a period of, from at least 2, at least 5, at least 10, at least 20, or at least 30 days. In some embodiments, the composition is provided on a daily basis comprising from 0.1 billion to 500 billion cfu of bacteria/day. In some embodiments, the level of LPS is reduced, as compared to a dysbiotic infant, by greater than 5%, 10%, 15%, 20%, 25%, 50%, 75%, 80%, or 85% by the treatment. In some embodiments, the level of LPS is reduced, as compared to a dysbiotic infant, to below 0.7 endotoxin units (EU)/mL, below 0.65 EU/mL, 0.60 EU/mL, or below 0.55 EU/mL. In some embodiments, the composition is provided on a daily basis comprising from 1 billion to 100 billion cfu/day, for example, the composition is provided on a daily basis comprising from 5 billion to 20 billion cfu/day. The bacteria can be chosen from bifidobacteria, Lactobacilli, and Pediococci, for example, the bifidobacteria can be *B. longum* or *B. longum* subspecies *infantis*. The MMO can be provided in a solid or liquid form at a dose from about 0.1-50 g/day, for example, 2-30 g/day or 3-10 g/d.

Levels of proinflammatory cytokines including, but not limited to, IL-2, IL-5, IL-6, IL-8, IL-10, IL-13, IL-22 and TNF-alpha, can be reduced relative to a dysbiotic infant, particularly by greater than 50%, greater than 60%, percent, greater than 70%, greater than 80%, greater than 90%, or greater than 95%. Reduction of the levels of proinflammatory cytokines including, but not limited to, IL-2, IL-5, IL-6, IL-8, IL-10, IL-13, and TNF-alpha, and/or increasing the levels of anti-inflammatory cytokines, in the gut of a mammal may be accomplished by treating that mammal with a daily dose of a medicament comprising a MMO and bacteria that selectively grows on that MMO, for a period of from at least 2, at least 5, at least 10, at least 20, or at least 30 days. The composition can be provided on a daily basis, and can include from 0.1 billion to 500 billion cfu of bacteria/day. For example, the composition can be provided on a daily basis comprising from 1 billion to 100 billion cfu/day, such as 5 billion to 20 billion cfu/day. The bacteria can be chosen from bifidobacteria, Lactobacilli, and Pediococci, such as *B. longum* or *B. longum* subspecies *infantis*. The MMO can be provided in a solid or liquid form at a dose from about 0.1-50 g/day, for example 2-30 g/day or 3-10 g/day.

Reduction of the risk of presenting certain metabolic disorders such as, but not limited to, Juvenile Diabetes (Type I), obesity, asthma, atopy, Celiac's Disease, food allergies and autism in a human, as compared to a dysbiotic infant, may be achieved by treating that human, beginning within the first 4 weeks of life, with a daily dose of a medicament comprising a MMO, and bacteria that selectively grows on that MMO, for a period of from at least 10, at least 20, at least 30, at least 60, at least 90, at least 120, at least 150, or at least 180 days. The risk can be reduced, as compared to a dysbiotic infant, by 20, 30, 40, 50, 60, 70, 80, or 90%. The composition that is provided can be given on a daily basis and can include from 0.01 billion to 500 billion cfu of bacteria/day, for example, from 1 billion to 100 billion cfu/day or from 5 billion to 20 billion cfu/day. The bacteria can be bifidobacteria, such as *B. longum* or *B. longum* subspecies *infantis*. The MMO can be provided in a solid or liquid form at a dose from about 0.1-50 g/day, for example, 2-30 g/day or 3-10 g/d. The composition can comprise the medicament and a food composition, and the food composition can include the complete nutritional requirements to support life of a healthy mammal wherein that mammal may be, but is not limited to, an infant, an adolescent, an adult, or a geriatric adult. The mammal can be a human. The bacteria and the MMO can be provided contemporaneously or separately at any time during 24 hr. The MMO could for example be provided along with an infant formula and the bacteria provided separately within 24 hr, 12 hr, 8 hr, 6 hr, 4 hr or 2 hr of consumption of the MMO.

A composition comprising mammalian milk of MMO and bifidobacteria in a concentration to provide a daily dose of from 0.1 billion to 500 billion cfu of bacteria/day can be provided. The MMO can be provided in a solid or liquid form at a dose from about 0.1-50 g/day, for example, 2-30 g/day or 3-10 g/d. The bifidobacteria can be *B. longum* or *B. longum* subspecies *infantis*. The composition can be a medicament for a mammal to prevent or treat a pathogenic bacterial overgrowth, which includes, but is not limited to, Enterobacteriaceae (e.g., one or more of *Salmonella, E. coli, Klebsiella*, or *Clostridium*). For example, the pathogenic bacterial overgrowth can include bacteria of *Clostridium difficile, Escherichia coli*, and/or Enterobacterium faecale.

In some embodiments, the mammalian milk is horse milk (mare's milk) and the recipient of the treatment is an infant horse (a foal). The medicament can further comprise a *lactobacillus* species including, but not limited to, *L. plantarum*. In some embodiments, the mammalian milk is human milk and the recipient of the treatment is an infant human. The infant human can be a premature infant with a body mass of less than 2.5 kg.

A simple, healthy microbiome can be described as the presence of greater than $10^8$ cfu/g stool of a single genus of bacteria (e.g., *Bifidobacterium*), more particularly, of a single subspecies or strain of bacteria (e.g., *B. longum* subsp. *infantis*). For example, up to 80% of the microbiome can be dominated by the single bacterial species such as *Bifidobac-* teria sp. or, more particularly, by the single subspecies of a bacteria such as *B. longum* subsp. *infantis*. A simple microbiome can also be described as the presence of greater than 20%, preferably greater than 30%, more preferably greater than 40%, greater than 50%, greater than 60%, greater than 70%, greater than 75%, greater than 80%, or greater than 90% of a single genus of bacteria (e.g., *Bifidobacterium*), more particularly, of a single subspecies of bacteria (e.g., *B. longum* subsp. *infantis*). This population has features of ecological competitiveness, resilience, persistence, and stability over time, as long as MMO are present.

The level of bifidobacteria in an infant can be determined using a device that measures pH. The inventors have determined that pH levels in a stool sample correlate well to the levels of bifidobacteria in a microbiome (e.g., an infant microbiome). In a healthy infant microbiome, the inventors discovered that bifidobacteria will generate at least 2.5 mmol of titratable acidity in the form of SCFA per gram of feces.

A fecal sample can be added to a mixture that includes a fixed concentration of NaOH and an indicator. The fecal sample and NaOH can be in a ratio of 200-400 mg fecal sample per mmol of NaOH. In some embodiments, a device is designed to match the range of titratable acid in a certain amount of fecal sample (i.e. 40-80 mg) to a fixed concentration of NaOH or other base such that the indicator changes color to discriminate high vs low *Bifidobacterium* fecal samples. The device can include a solution that includes 0.1M NaOH. KOH or any other appropriate base can also be used in the invention. The solution that includes 0.1M NaOH can also include deionized water and/or ethanol or other suitable alcohols such as but not limited to methanol, propanol, and isopropanol. The device can include a reading window and a sampling devise which can aide the user in providing a precise amount of the fecal material (e.g. 40 mg). The device can include a filter to remove the particulate matter. The fecal sample and indicator can be added contemporaneously into the device. In some embodiments, the indicator can be in a vessel into which the fecal sample and solution are introduced. The device can include a reading window to view the colorimetrc reaction between the fecal sample, indicator and NaOH. If the device contains an indicator, such as phenolphthalein in dilute ethanol whose color changes in the range of 8.2, the color of the resulting composition can indicate a threshold level of bifidobacteria in the sample.

If the mixture of the fecal sample plus indicator phenolphthalein and NaOH has a pH of 8.5 or above, the fecal sample has a fecal pH of 6.0 or above and the sample would be described as low bifidobacteria. The pH of the composition is less than 8.5, the fecal sample would have had a pH of 6.0 or less and the sample would be described as high in bifidobacteria. Due to the discovery of the relationship between fecal pH and bifidobacteria levels, the indication of fecal pH levels indicates the bifidobacteria levels in the sample. Thus, a fecal sample with a low level of bifidobacteria will remain pink if phenolphthalein is the indicator. A fecal sample with a high level of bifidobacteria will turn the indicator from pink to yellow.

Alternatively, a device that includes an indicator that indicates pH directly can be utilized with a fecal sample that may be deproteinated and/or filtered. Indicators such as, but not limited to, chlorophenol red (yellow to violet), transition from one color to another around pH 6.0 and may be used to visually discriminate a high bifidobacteria fecal sample from a low bifidobacteria fecal sample. A pH of 6.0 or below demonstrates that the sample has high levels of bifidobacteria. The device design may provide a window that gives a positive (high bifidobacteria) and negative (low bifidobacteria) sign to the user. Alternatively, users are provided a color card to match Bif level to test result. In other embodiments, an optical reader may be used to establish the colorimetric change associated with the pH differential.

EXAMPLES

Example 1: Preparation of additional HMO-selective bacteria. A sample of feces is obtained from a vaginally delivered breast-fed baby, diluted with sterile saline and mixed to form a suspension of live bacterial cells that are representative of those in that fecal sample. An aliquot of this suspension is then transferred to liquid growth medium comprising deMan Rogosa Sharpe (MRS) media wherein the sole carbon source is made up of human milk oligosaccharides (HMOs) at a concentration of from 5-20 g/L (the "HMO Medium"), and the cultures are grown in an anaerobic chamber for 16-72 hr allowing the selective enrichment of bacterial strains that can utilize the HMOs as a selective carbon source. The consortia from these enrichment cultures are then diluted and transferred to agar plates also containing HMO as the sole carbon source, and the plates are incubated for an additional 24-72 hr in an anaerobic environment. Individual pure colonies are then picked and transferred to microtiter plates with wells containing 50-200 uL of HMO Medium and these "Microcultures" are incubated for another 16-48 hr in an anaerobic chamber. Finally, 20 uL samples from each individual Microculture are transferred to a single well in a 96 well microplate containing 200 uL of HMO Medium (a "Miniculture"), and the growth of each individual clone is monitored hourly by optical density of the Minicultures over a period of 72 hr. Lead candidates identified by robust growth are then checked for identity using 16S RNA sequencing and phenotypic testing.

Example 2. Trial with Breast-fed Infants. This trial was designed to show the effect of probiotic supplementation with bifidobacteria in healthy term nursing infants compared to an unsupplemented group. A dry composition of lactose and activated *Bifidobacterium longum* subsp. *infantis* was prepared starting with the cultivation of a purified isolate (Strain EVC001, Evolve Biosystems Inc., Davis, CA, isolated from a human infant fecal sample) in the presence of BMO according to PCT/US2015/057226. The culture was harvested by centrifugation, freeze dried, and the concentrated powder preparation had an activity of about 300 Billion CFU/g. This concentrated powder was then diluted by blending with infant formula grade lactose to an activity level of about 30 Billion CFU/g. This composition then was loaded into individual sachets at about 0.625 g/sachet and provided to breast-fed infants starting on or about day 7 of life and then provided on a daily basis for the subsequent 21 days.

This was a 60-day study starting with infants' date of birth as Day 1. Before postnatal day 6, women and their infants (delivered either vaginally or by cesarean-section), were randomized into an unsupplemented lactation support group or a *B. infantis* supplementation plus lactation support group. Infant birthweight, birth length, gestational age at birth, and gender were not different between the supplemented and unsupplemented groups. Starting with Day 7 postnatal, and for 21 consecutive days thereafter, infants in the supplemented group were given a dose of at least $1.8 \times 10^{10}$ cfu of *B. infantis* suspended in 5 mL of their mother's breastmilk, once daily. Because the provision of HMO via breastmilk was critical for supporting the colonization of *B. infantis*, all participants received breast feeding support at the hospital and at home and maintained exclusive breast feeding through the first 60 days of life.

Infant fecal samples were collected throughout the 60-day trial. Mothers collected their own fecal and breastmilk samples as well as fecal samples from their infants. They filled out weekly, biweekly and monthly health and diet questionnaires, as well as daily logs about their infant feeding and gastrointestinal tolerability (GI). Safety and tolerability was determined from maternal reports of infants' feeding, stooling frequency, and consistency (using a modified Amsterdam infant stool scale—watery, soft, formed, hard; Bekkali et al. 2009), as well as GI symptoms and health outcomes. Individual fecal samples were subjected to full microbiome analysis using Illumina sequencing based on 16S rDNA and qPCR with primers designed specifically for *B. longum* subsp *infantis* strain.

Results

*B. infantis* was determined to be well-tolerated. Adverse events reported were events that would be expected in normal healthy term infants and were not different between groups. Reports specifically monitored blood in infant stool, infant body temperature and parental ratings of GI-related infant outcomes such as general irritability, upset feelings in response to spit-ups and discomfort in passing stool or gas, and flatulence. Furthermore, there were no differences reported in the use of antibiotics, gas-relieving medications, or parental report of infant colic, jaundice, number of illnesses, sick doctor visits and medical diagnoses of eczema.

Figure 2A:
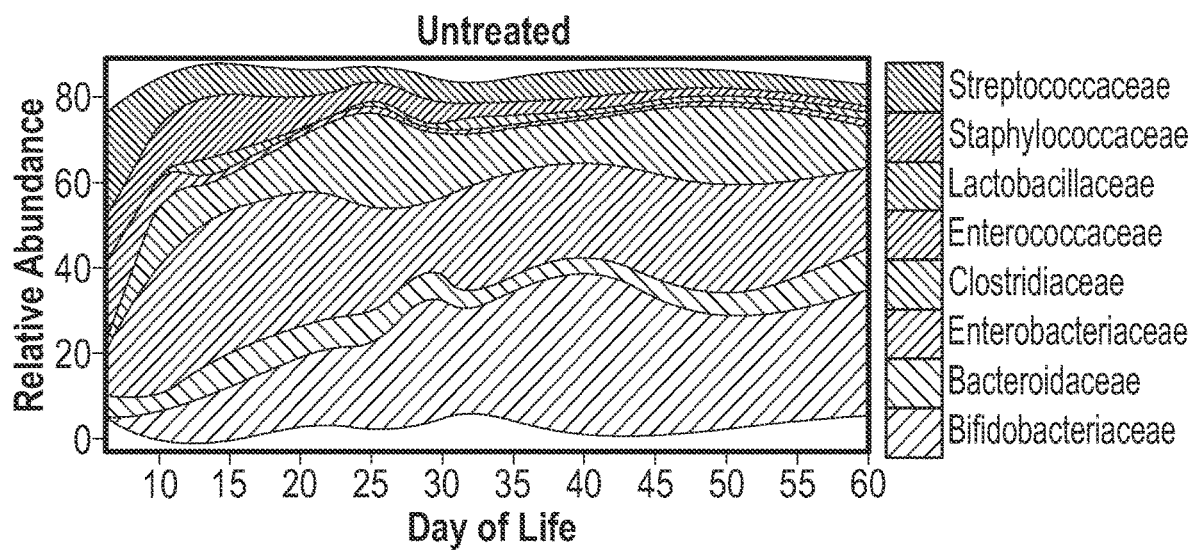
FIG. 2A. Abundances of different genera of intestinal bacteria in an untreated C-section baby over the study period (Day 6 to 60 of life).
Figure 2B:
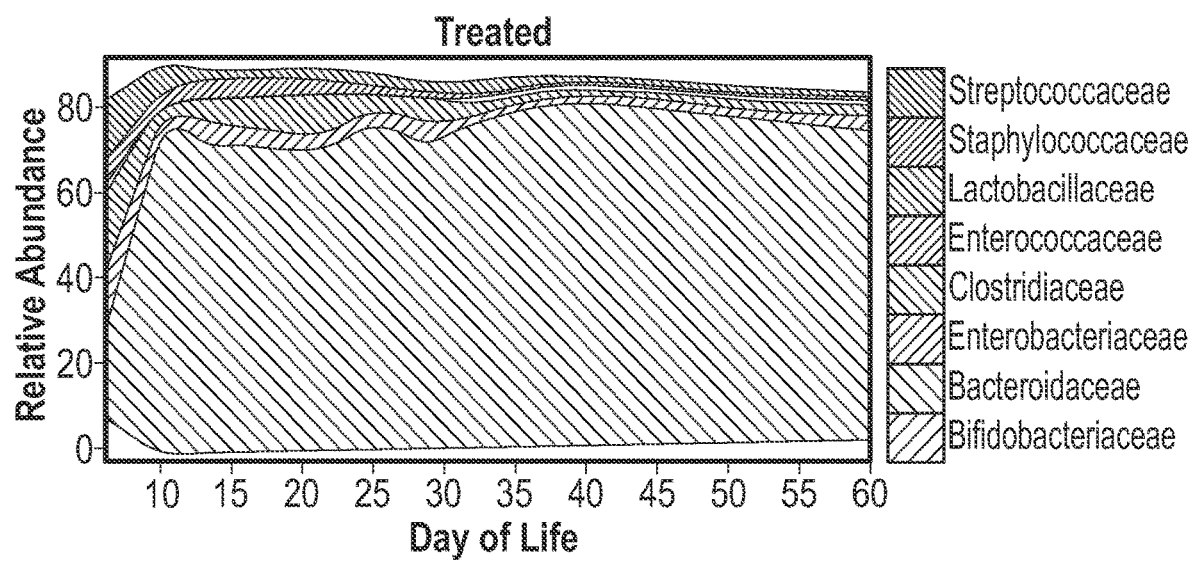
FIG. 2B. Abundance of different genera of intestinal bacteria in a C-section baby treated from Day 7 to 28 with *B. longum* subsp. *infantis*.

The *B. infantis* supplemented infants had a gut microbiome fully dominated (on average, greater than 70%) with *B. longum* subsp *infantis* regardless of the birthing mode (vaginal or C-section). This dominance continued even after supplementation ended (Day 28) as long as the infant continued to consume breast milk indicating that *B. infantis* was colonizing the infant gut to levels higher than $10^{10}$ cfu/g feces (FIG. 1). Furthermore, those infants that were colonized by the *B. longum* subsp *infantis* also had much lower levels of proteobacteria and enterococci (including *Clostridium* and *Escherichia* species) (FIG. 2).

Unsupplemented infants (i.e., infants receiving the standard of care—lactation support but no supplementation of *B. infantis*) did not show *B. infantis* levels above $10^6$ cfu/g (i.e., the limit of detection) in their microbiome and there were no significant differences in the microbiomes between C-section and vaginally delivered infants. Eighty percent (8 of 10) unsupplemented infants delivered by C-section had no detectable *Bifidobacterium* species and fifty-four percent (13 of 24) of the vaginally delivered infants had no detectable *Bifidobacterium* species by day 60. Further analysis of the thirteen unsupplemented infants that had some detectable bifidobacteria, found that the species were primarily B. long urn subsp *longum, B. breve* and *B. pseudocatenulatum*. No detectable *B. longum* subsp. *infantis* was found in any of the unsupplemented infants in the study.

Figure 3:
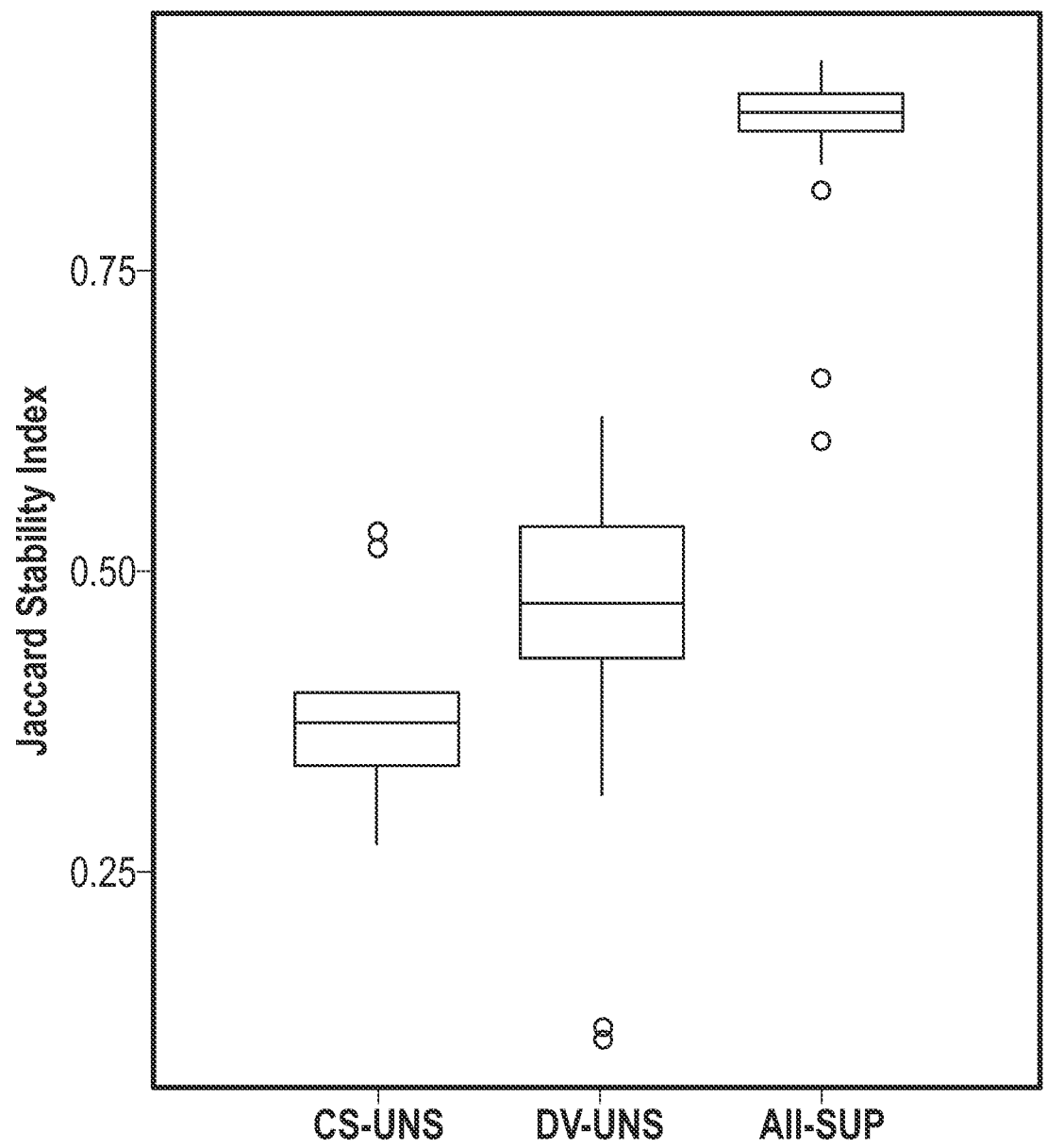
FIG. 3. Jaccard stability index of unsupplemented infants delivered by C-section (CS-UNS) or delivered vaginally (DV-UNS) compared to *B. infantis* supplemented infants which included both C-section and vaginally-delivered infants together (All-SUP).

The changes in the infant gut ecology associated with the *B. infantis* supplementation and its subsequent domination by *B. infantis* to over 80% resulted in a significant increase in ecological stability of the microbiome. The Jaccard Stability Index is a metric of ecosystem stability in that it can be regarded as a measure of the changeability of a complex system. See, e.g., Yassour M, et al. (2016) Natural history of the infant gut microbiome and impact of antibiotic treatment on bacterial strain diversity and stability. Science Translational Medicine 8(343):343ra81-343ra81. The Jaccard stability index for the microbiome of the unsupplemented, C-section delivered infants was significantly lower than that of the unsupplemented vaginally-delivered infants (FIG. 3). However, all the *B-infantis* treated infants, whether delivered vaginally or by C-section, had an exceptionally high ecological stability which reflected a very stable microbial composition.

Figure 4:
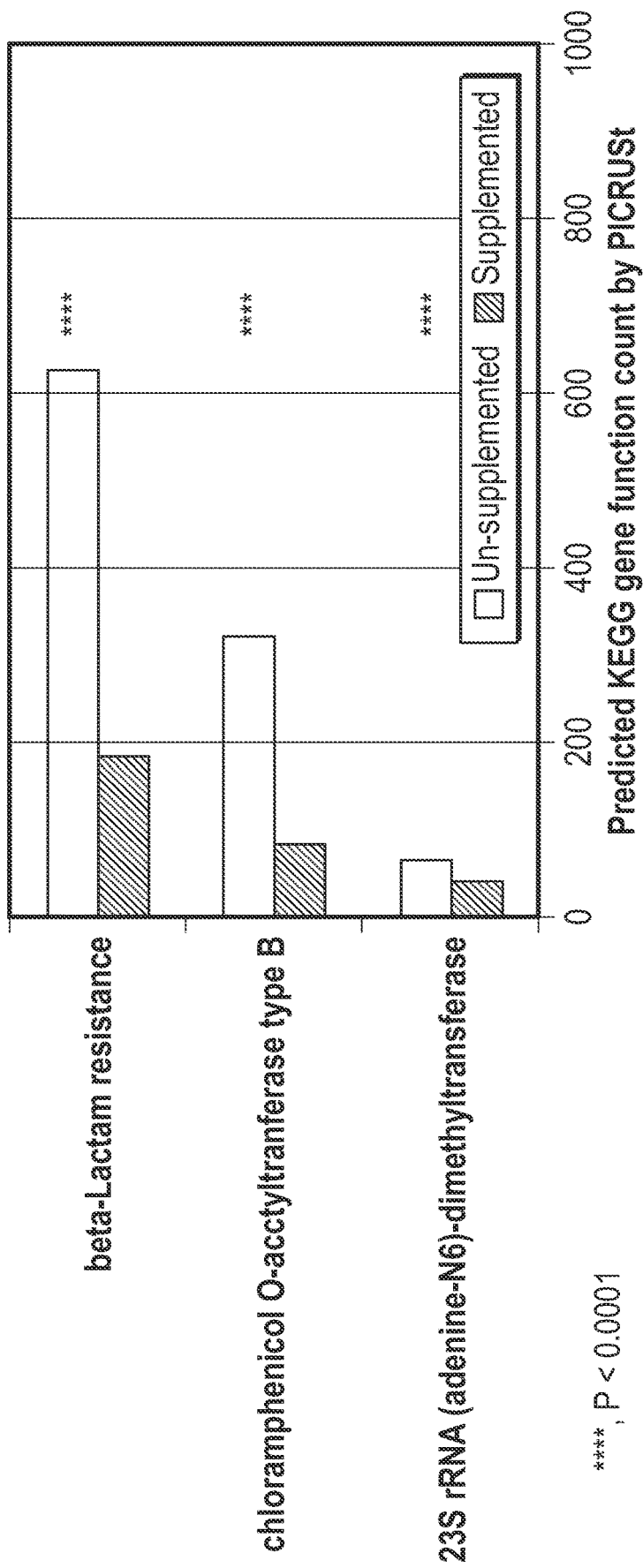
FIG. 4. Predictive antibiotic (AB) resistance gene load in fecal samples taken from unsupplemented (white bars) or supplemented (black bars) infants.

Two different methods were used to examine the fecal samples for antibiotic resistance gene load present in the total microbiome of unsupplemented vs. *B. infantis* supplemented infants: 1) the Pfaffl method for relative abundance of a gene sequence (compared to 16S rRNA); and 2) a machine learning approach. In *B. infantis* supplemented infants, erythromycin resistance genes (ermB) were reduced by about half in supplemented infants compared to unsupplemented infants using the Pfaffl Method for analyzing qPCR results (p=0.0258). To functionally classify the genes in fecal samples from unsupplemented or *B. infantis* supplemented groups, the 16S rRNA amplicon libraries generated were first organized into normalized, operational taxonomic unit (OTUs). PICRUSt, a publicly available bioinformatics freeware (picrust.github.io/picrust), was used to produce a table containing predicted gene classification of all the genes present. The genes were assigned using the Kyoto Encyclopedia of Genes and Genomes (KEGG) database (Kanehisa et a., 2000). Differences of predicted gene content in KEGG categories among samples were statistically analyzed using a Kruskal-Wallis one-way ANOVA with Bonferroni correction to adjust p-values (Theodorsson-Norheim et al., 1986). Among the KEGG Orthologies identified, chloramphenicol 0-acetyltransferase type B, was significantly increased in the unsupplemented samples (p=5.50E-44; Bonferroni). Levels of the antibiotic resistance gene annotated as 23S rRNA (adenine-N6)-dimethyltransferase were significantly higher in the unsupplemented infants (p=1.32E-06; Bonferroni) than the supplemented infants. An entire group of antibiotic resistance genes were identified as beta-Lactam resistance genes and these genes were three times higher in the unsupplemented infants compared to the *B. infantis* supplemented infants (p=4.94e-56; Bonferroni) (FIG. 4).

Figure 5:
FIG. 5. Mean concentration of fecal HMO (+/−SD, mg/g) in infant stools collected at baseline (Day 6; pre-supplementation) and at the end of supplementation (Day29; post-supplementation). Dark grey bars represent the *B. infantis* supplemented group.

The concentration of HMOs in infant feces was analyzed by liquid chromatography-mass spectrometry (LC-MS). The mean fecal HMO concentration in samples from *B. infantis* supplemented infants (4.75 mg/g) was 10-fold lower than in samples from unsupplemented infants (46.08 mg/g, P<0.001 by Tukey's multiple comparison test; FIG. 5).

When infant fecal samples were analyzed by LC-MS, *B. infantis* supplementation significantly increased fecal organic acids—particularly lactate and acetate. Other SCFAs (formate, propionate, butyrate, isovalerate, isobutyrate, and hexanoate) were in low abundance in the infant stool. Supplemented infants had significantly greater fecal organic acid concentrations than unsupplemented infants (126.55 µmol/g vs 52.02 µmol/g). The median lactate to acetate ratio of *B. infantis*-supplemented infants (0.73), was near the molar ratio of the "bifid shunt" (0.67), whereas low-bifidobacteria samples (the unsupplemented group) had a lactate to acetate ratio of 0.26 (P<0.0001, Mann-Whitney test).

Figure 6:
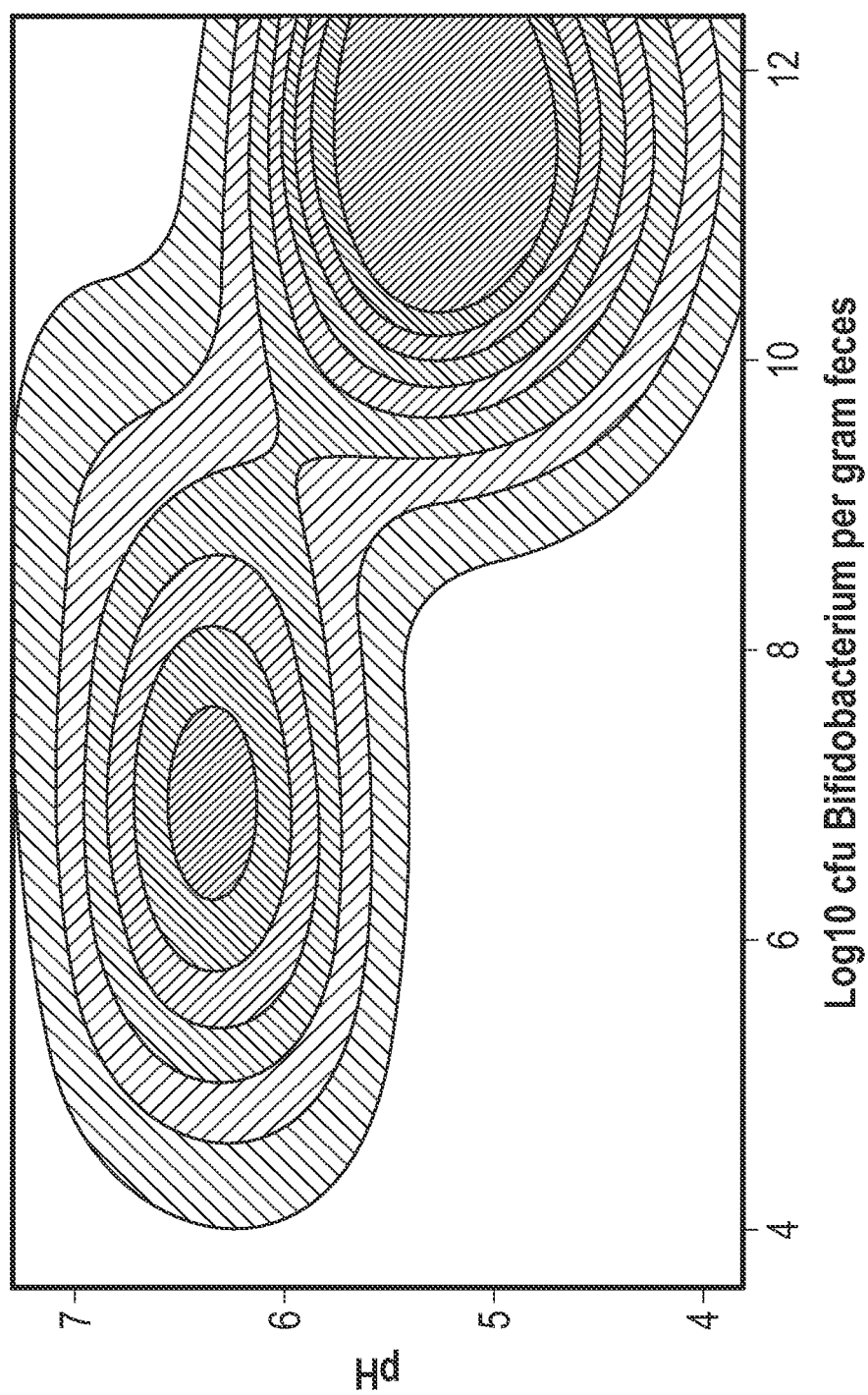
FIG. 6. 2D density plot of all samples comparing total *Bifidobacterium* measured by qPCR ($Log_{10}$ CFU/g feces) with fecal pH.

Monitoring pH in infant fecal samples showed a correlation between pH and the abundance of bifidobacteria in the sample. The mean fecal pH of the unsupplemented group was 5.97, while the feces from *B. infantis*-colonized infants had a significantly lower mean pH of 5.15 at day 21 postnatal (P<0.0001, Mann Whitney test)(FIG. 6A). The pH of feces from that portion of unsupplemented infants who had no detectable bifidobacteria at all was 6.38, which was statistically higher than either of the other two groups (P<0.0001 Mann Whitney test). Overall, when compared across infants, absolute bifidobacteria populations in infant stools were negatively correlated with fecal pH (Spearman's p=−0.62, P<0.01) and demonstrated a bimodal distribution of fecal pH measurements that mirrored the abundance of bifidobacteria (FIG. 6). Comparing weighted UniFrac distance matrixes, pH was a significant discriminator of sample community composition (Mantel Test, =0.32, P=0.002).

Figure 7:
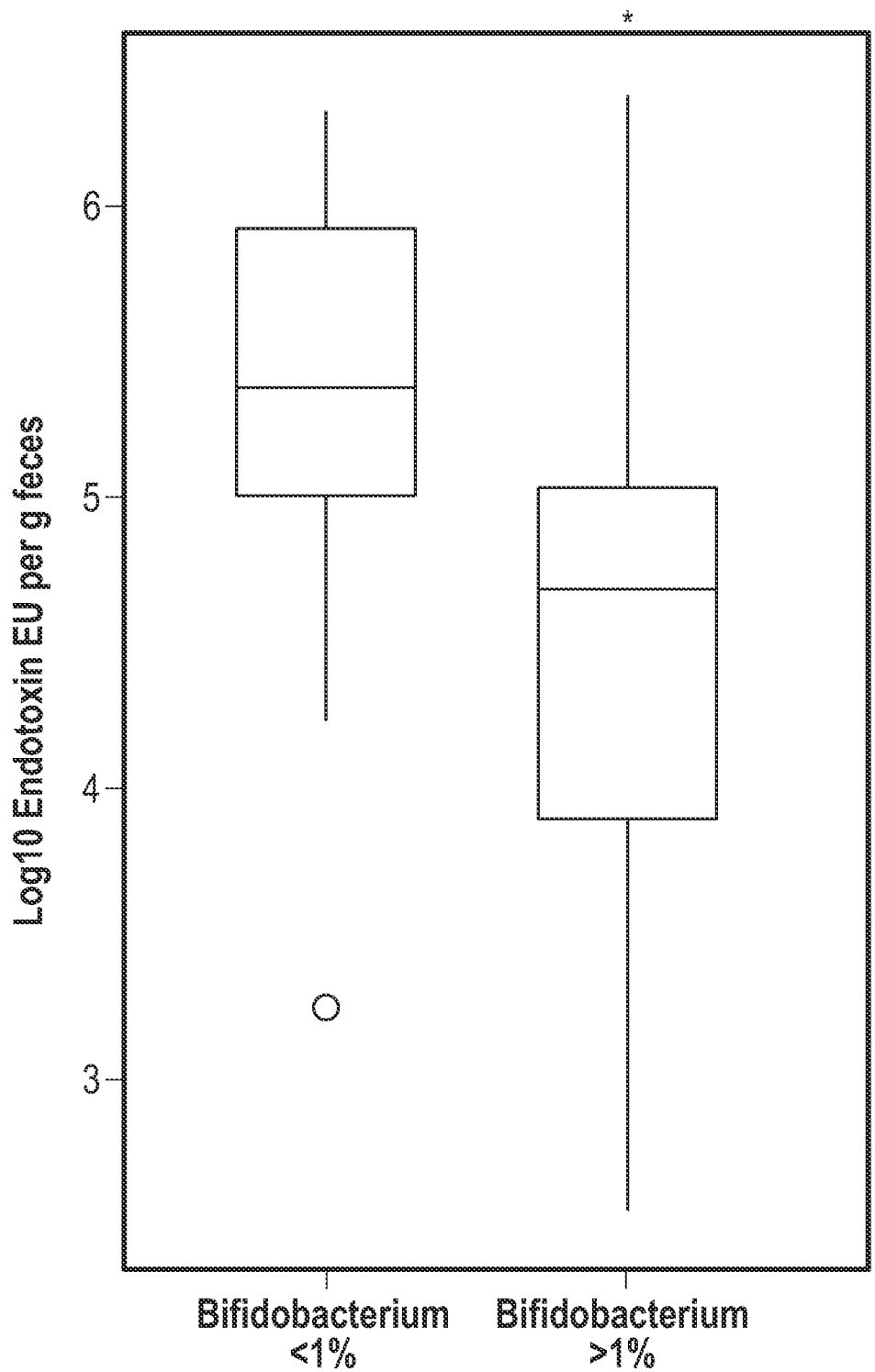
FIG. 7. Box plot of endotoxin levels (Log EU/ml) in fecal samples from unsupplemented infants devoid of all bifidobacteria (*Bifidobacterium*-naïve) vs. fecal samples from infants supplemented with *B. infantis* and replete with bifidobacteria (High Bifidobacteria).

Measuring endotoxin (LPS) in the stool samples showed higher endotoxin in the unsupplemented infants (control) than in the supplemented infants (FIG. 7). The endotoxin load was nearly 4-fold lower in infants colonized at high levels with *B. infantis* (>50% Bifidobacteriaceae) compared with endotoxin levels in infants with low levels of bifidobacteria, despite a high inter-individual variation (4.64 vs 5.15 $Log_{10}$ EU/mL, P=0.0252, Mann-Whitney U). Endotoxin was significantly correlated with Enterobacteriaceae relative abundance (P>0.0001, R=0.496), but not Bacteroidaceae, the second most abundant Gram-negative family found in the present study (P=0.2693), and endotoxin concentrations were inversely correlated with Bifidobacteriaceae abundance (P>0.001, R=−0.431). Thus, infants that had high levels of *B. infantis* colonization had lower endotoxin levels as compared to infants that did not have high levels of *B. infantis* colonization Fecal cytokines in stool samples were measured at day 14 of supplementation. Such cytokines include pro-inflammatory cytokines like IL-8 and TNF-α. A typical immune response to pathogens involves the rapid activation of pro-inflammatory cytokines (e.g., IL-8 and TNF-α) that serve to initiate host defense against microbial invasion. Since excess inflammation can give rise to systemic disturbances harmful to the host, the immune system has evolved parallel anti-inflammatory mechanisms that serve to curb the production of pro-inflammatory molecules to limit tissue damage. Interleukin 10 (IL-10) is such a molecule that can limit host immune response to pathogens and prevent inflammatory and autoimmune pathologies. Elevated levels of pro-inflammatory IL-8 and TNF-α coupled with elevated levels of IL-10, blunting the inflammatory response, are indicative of a significant inflammatory battle going on within the gut of the unsupplemented infants (Table 1). In contrast, in the infants supplemented with *B. infantis*, the pro-inflammatory cytokines are minimized as are the levels of IL-10, indicating that the colon of these infants is in a far calmer state with respect to inflammatory responses.

TABLE 1

Levels of fecal cytokines in fecal samples from unsupplemented infants (−*B. infantis*) and infants supplemented (+*B. infantis*).

| Cytokine | −*B. infantis* | +*B. infantis* | P Value |
| --- | --- | --- | --- |
| IL-8 (pg/mL) | 1.01 | 0.07 | 0.0378 |
| IL-10 (pg/mL) | 329.78 | 23.68 | 0.0398 |
| TNF-a (pg/mL) | 151.16 | 21.63 | 0.0686 |

Figure 8:
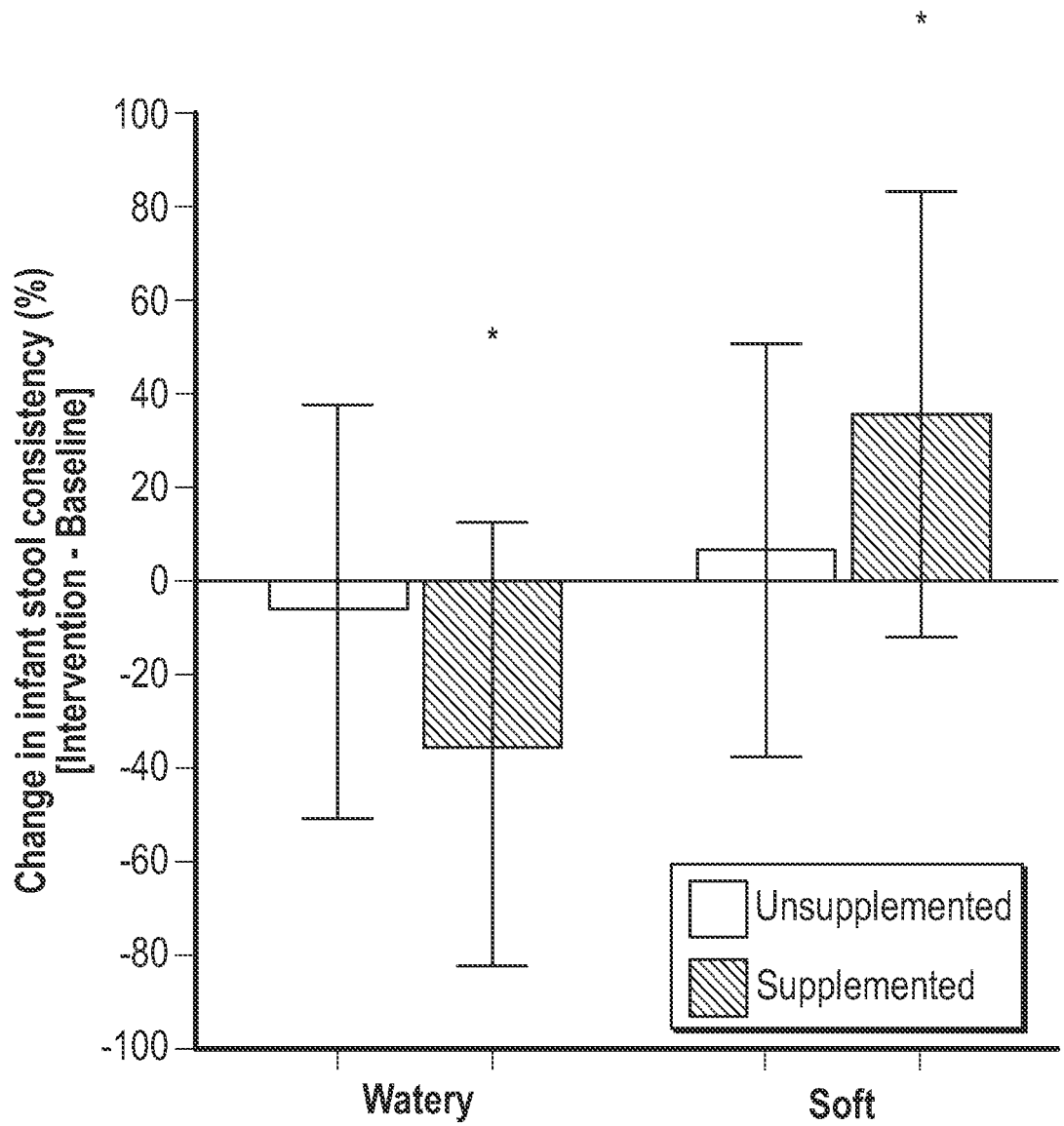
FIG. 8. Percent change in the infant stool consistency for the untreated (grey bars) and *B. infantis*-treated (black bars) groups between Intervention and Baseline and between Post-intervention and Intervention. (*) P<0.05.

Infant stooling (number and consistency) was recorded in this study as a metric of GI function (Weaver et al. 1988). The number of infant bowel movements at Baseline was the same between the supplemented (mean, 4.0/d; range (0.80-9.6)) and unsupplemented groups (mean, 3.9/d; range (0.80-7.6)) but was significantly (P<0.0005) different during the Intervention (supplemented: mean, 3.2/d, range (0.52-7.2); unsupplemented: mean, 5.5/d, range, (2.6-10.6)) and Post-intervention (supplemented: mean, 1.7/d, range (0.30-4.8); unsupplemented: mean, 4.4/d; range, (0.97-9.9)) periods (FIG. 8). The mean number of bowel movements were not only different between groups (P<0.01) but also different across time within each group (P<0.0005). There was a significant time effect (P<0.01), time x intervention interaction (P<0.0005) and intervention effect (P<0.0005) for the daily number of infant stools. The number of infant stools significantly increased from Baseline (P<0.0005) for infants in the unsupplemented group and decreased from Baseline (P<0.05) for infants in the supplemented group and significantly decreased during the Post-intervention period for both groups (P<0.0005). Parity was unrelated to the number of reported mean number of bowel movements/d across all three time periods.

To examine the quality of infant stool, mothers reported the consistency of the first bowel movement their infants produced each day using a validated stool consistency rating tool for infants (Bekkali et al. 2009). The proportion of each stool type (watery, soft, formed and hard) over each time period was calculated for each infant as the number of days each type was reported divided by the total number of days per each time period. The majority (95%) of the mothers rated stools as watery or soft. Maternal reports for the proportion of watery stools during the intervention period was lower for infants in the supplemented vs. unsupplemented group (0.20 vs. 0.33) and higher for the number of soft stools (0.79 vs. 0.67). The change in the percent of watery and soft stools was significantly different between the two groups. The percent of watery stools decreased from Baseline to the Intervention period in infants in the supplemented group by 36% but only 7% in the unsupplemented group (P<0.05). As expected, the percent of soft stools increased by 36% from Baseline to the Intervention period in the supplemented group but only increased by 7% in the unsupplemented group (P<0.05) (FIG. 8).

Overall, the unsupplemented infant had average stool frequency of 4.0/day, of which 33% were watery stools, and average stool pH=6. The supplemented baby had average stool frequency of 1.8/day, of which only 20% were watery stools, and the stool pH was reduced to 4.5. Endotoxin and other inflammatory markers, including IL-8, IL-10, IL-6, and TNFa, appeared to be reduced in the infants colonized with the *B. longum* subsp *infantis* such that the gut ecology was found to be in an anti-inflammatory condition. The supplementation of *B. infantis* also facilitates maturation of the gut mucosa as supported by the data showing less frequent and more mature stool consistency in the breast-fed infants supplemented with *B. infantis*.

This experiment demonstrates that non-dysbiotic infants can be identified as compared to dysbiotic infants by the following: (a) an increased in the lactate:acetate ratio to around 2:3 in the feces; (b) decreased frequency of bowel movements as compared to a dysbiotic infant; (c) more mature stool consistency (i.e., more firm and/or less watery); (d) decreased pro-inflammatory cytokines (e.g., IL-8 and IL-10) by around 10× in the feces; (e) decreased inflammatory LPS by around 4× in the feces; (f) decreased pathogenic microbe levels in the feces; (g) decreased antibiotic resistance gene load by around 3× in the feces; (g) titratable acidity above 2 mmol/g feces, preferably above 5 mmol/g feces; (h) bifidobacteria levels of greater than $10^6$, preferably greater than $10^8$, more preferably greater than $10^9$ or $10^{10}$ in the feces; (i) *B. infantis* levels of greater than $10^6$, preferably greater than $10^8$, more preferably greater than $10^9$ or $10^{10}$ in the feces; and/or (j) decreased HMO levels present in the feces of at least an order of magnitude, compared to dysbiotic infants. These indicators may be expected to distinguish dysbiotic infants from non-dysbiotic infants across all mammals, not just human infants.

Example 3: Trial with formula-fed infants. A dry composition of lactose and *Bifidobacterium longum* subsp. *infantis* (Strain EVC001, Evolve Biosystems Inc., Davis, CA isolated from a human infant fecal sample) produced in an activated form by cultivation in the presence of BMO according to PCT/US2015/057226, is prepared so that it has an activity level of about 15 Billion CFU/g. This composition is combined with a HMO or BMO syrup prepared by defatting a sample of human milk by centrifugation, preparing a HMO concentrate by microfiltration where milk proteins are removed, and then concentrating the filtrate under vacuum to a water content of less than 0.5. This HMO syrup is combined with the activated *B. longum* to provide a composition of 2.0 g HMO with a *B. infantis* titer of $5 \times 10^9$ CFU/dose. The resulting syrup is packaged in foil-lined stick packs wherein one dose represents about 2 g. Alternatively, the medicament can be prepared in a dry form and packaged in stick packs or other forms of sachet. The contents of individual dose packs are provided to formula-fed or mixed-fed infants on or about day 7 of life and then on a daily basis for the subsequent 180 days. Infant fecal samples are collected throughout the trial and subjected to full microbiome analysis using Illumina sequencing based on 16S rRNA and qPCR with primers designed specifically for B. long urn subsp *infantis*. The supplemented infants have a significantly higher level of *B. infantis* than the unsupplemented infants whether vaginally delivered or delivered by C-section. When the infants terminate supplementation with HMO plus *B. infantis*, the levels of *B. infantis* in the gut drop off precipitously. Those infants that were colonized by the *B. longum* subsp *infantis* have much lower levels of Proteobacteria (including *Clostridium* and *Escherichia* species). Infant fecal samples from the supplemented infants have acetic acid levels about 100-fold higher than the unsupplemented infants. Other pro-inflammatory markers including IL-8, TNFa, and PPARa and PPARg are reduced in the supplemented infants indicating that the gut ecology is in an anti-inflammatory condition.

Example 4: Equine Trial. A major horse breeding stable with over 70 pregnant thoroughbred mares had an outbreak of severe hemorrhagic diarrhea among foals born to the mares in that stable. These animals were found to be culture- and toxin-positive for *Clostridium difficile*. Seventeen foals were born during the initiation of the outbreak, of which fifteen animals became ill and required intervention, according to the standard of care (i.e., antibiotic treatment) and two died. Another eight animals were born and initially treated with a formulation comprising $6 \times 10^9$ CFU *Bifidobacterium longum* subspecies *infantis* (Strain EVBL001, Evolve Biosystems Inc., Davis, CA) per kg bodyweight and $5 \times 10^9$ CFU of *Lactobacillus plantarum* (Strain EVLP001, Evolve Biosystems Inc., Davis CA) diluted in cultured bovine milk which contained BMO. All treated animals were given doses immediately at birth and twice per day thereafter for 4 days. In total, twenty five treated foals, six did not develop disease. Two foals, who were dosed starting at 12 hours of life rather than immediately at birth, developed a mild infection by *Clostridium difficile* but recovered within 8 hr compared to the standard recovery time of >24 hr for sick animals given the standard of care. No adverse events were recorded among the animals and the dosages were well tolerated. A Fisher's exact test of the two populations (Standard of Care and Probiotic treated) yields a significant difference in incidences of *C. difficile* infection (p=0.0036) (Table 2).

TABLE 2

Summary of Outcome Data for Foals.

| | Outcomes (# animals) | | |
|---|---|---|---|
| Treatment | Healthy | Sick | Dead |
| No treatment at birth | 9 | 19 | 2 |
| Prophalyatic *B.infantis* + *L. plantarum* at birth | 25 | 4 | 0 |

| | Outcomes (Duration of symptoms) | |
|---|---|---|
| Treatment | Less than 12 hours | Greater than 24 hours |
| No treatment at birth | 0 | 21 |
| Prophalyatic *B.infantis* + *L. plantarum* at 12 hours | 4 | 0 |

Although the treatment option where the animals were dosed at 12 hours of life failed to significantly reduce incidence of diarrhea, the severity (duration) was dramatically shortened to 12 hours or less (p=0.0074; Fisher exact test, comparing populations of diarrheal foals segregated by duration of diarrhea). The second option, dosing at birth, significantly reduced the incidence of diarrhea (p<0.0001). All animals were dosed at birth with 6.6 mg/kg of ceftiofur (Excede), and this did not affect health outcome, related to diarrhea. Furthermore, none of the 25 animals treated with the composition of the instant invention developed foal heat diarrhea, which typically affects >50% of animals, and requires treatment in approximately 10% of cases (Weese and Rousseau 2005). If a >50% risk is extrapolated to a hypothetical population of 8 animals to match the 8 observed; this yields a significant reduction in foal heat diarrhea (p=0.0256). Quantitative PCR of foal fecal samples obtained during the study showed 1000-fold increase in the abundance (on average) of bifidobacteriva (all species) after supplementation. Using the Pfaffl method for relative abundance of a gene sequence (compared to 16S rRNA), it was determined that resistance genes for gentamycin and tetracycline (aac6-aph2 and tetQ, respectively) were both significantly reduced by about 25-30% in treated foals compared to control foals. Analysis of fecal samples also revealed at 16-fold increase in SCFA after supplementation, comprised mostly of an increase in acetate.

Figure 9:
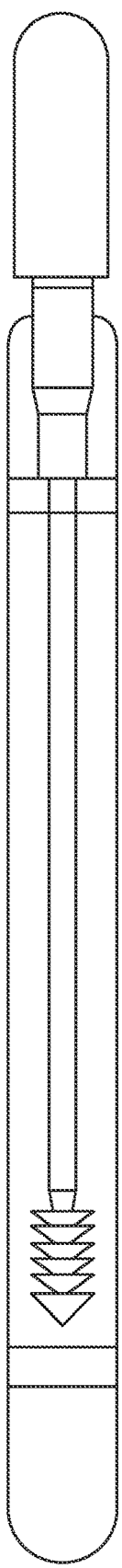
FIG. 9. An exemplary device to distinguish between infants with a microbiome replete in bifidobacterial from those depleted in bifidobacterial from a stool sample.

Example 5: Determining *Bifidobacterium* levels in infant stool samples. A fresh stool sample was collected from an unsupplemented infant and from a *B. infantis* supplemented infant. The stool samples were collected from soiled diapers using a collection wand that when rolled over the stool sample collected between 40-80 mg of feces. The wand is then placed in a chamber and 800 ul phenopthalein/ethanol/ 0.1 M NaOH solution was added and gently shaken. The phenopthalein/NaOH fecal composition was filtered into a second chamber to remove particulate matter. The clarified sample was viewed though the reading window. An exemplary device to the one used is shown in FIG. 9. In the samples from unsupplemented infant, the reading window was pink indicating that the original fecal pH was above 6 and that this infant has a low bifidobacteria microbiome. In contrast, the result from the *B. infantis* supplemented infant was yellow indicating that the infant microbiome contains high bifidobacteria and the fecal pH was less than 6.

The invention claimed is:

1. A method of controlling the intestinal environment of a mammal by increasing and/or maintaining a level of short chain fatty acids (SCFA) or organic acids in the mammal's colon, the method comprising:
   a) selecting a dysbiotic mammal having a lactate:acetate ratio of less than 2:3 in its feces; and
   b) administering to the mammal a bacterial composition comprising bacteria capable of colonization of the mammal's colon; and
   c) adding one or more mammalian milk oligosaccharides (MMO) to the mammal's diet as necessary to maintain MMO as at least 10% of total dietary fiber in the mammal's diet.

2. The method of claim 1, wherein the method reduces antibiotic resistance gene load of at least one gene in the mammal's colon, wherein the antibiotic resistance gene load of said at least one gene is reduced by greater than 25%, 50%, 75%, 80%, or 85%, and/or wherein pathogenic bacteria in the feces is reduced by 20%, and/or wherein the firmness of stool composition of the mammal is increased.

3. The method of claim 1, wherein the bacterial composition is provided to the mammal contemporaneously or within 2 hours of the addition of the MMO.

4. The method of claim 1, wherein the bacterial composition and/or MMO are administered daily or for a period of at least 2, at least 5, at least 10, at least 20, at least 30, at least 60, at least 90, at least 120, at least 150, or at least 180 days.

5. The method of claim 1, wherein the mammal is receiving MMO at a dose representing over 25%, over 40%, or over 50% of the total dietary fiber.

6. The method of claim 1, wherein the MMO consists of carbohydrate polymers found in mammalian milk which are not metabolized by any combination of digestive enzymes expressed from mammalian genes.

7. The method of claim 1, wherein the MMO is added in a food composition.

8. The method of claim 7, wherein the food composition comprises mammalian milk, mammalian milk derived product, and/or mammalian donor milk.

9. The method of claim 7, wherein the food composition comprises infant formula, a milk replacer, an enteral nutrition product, and/or meal replacer for the mammal, or wherein the food composition is sufficient to sustain growth of the mammal.

10. The method of claim 1, wherein the bacterial composition comprises bacteria that can grow in an anaerobic culture whose sole carbon source is MMO.

11. The method of claim 1, wherein at least one species of the bacterial composition comprises bacteria capable of expressing genes for a transporter that internalizes one or more MMOs intact.

12. The method of claim 1, wherein the bacterial composition comprises bacteria of a genus selected from the group consisting of Bifidobacteria, *Lactobacillus* and *Pediococcus*.

13. The method of claim 1, wherein the bacteria are *B. adolescentis, B. animalis, B. animalis* subsp. *animalis, B. animalis* subsp. *lactis, B. bifidum, B. breve, B. catenulatum, B. longum, B. longum* subsp. *infantis, B. longum* subsp. *longum, B. pseudocatanulatum, B. pseudolongum, L. acidophilus, L. antri, L. brevis, L. casei, L. coleohominis, L. crispatus, L. curvatus, L. fermentum, L. gasseri, L. johnsonii, L. mucosae, L. pentosus, L. plantarum, L. reuteri, L. rhamnosus, L. sakei, L. salivarius, P. acidilactici, P. argentinicus, P. claussenli, P. pentosaceus, P. stilesii L. paracasei, L. kisonensis, L. paralimentarius, L. perolens, L. apis, L. ghanensis, L. dextrinicus, L. shenzenensis, L. harbinensis, P. parvulus*, or *P. lolii*.

14. The method of claim 1, wherein the mammal is a pre-term infant or a term infant.

15. The method of claim 1, wherein the mammal is an infant born by C-section.

16. The method of claim 1, wherein the mammal is a dysbiotic infant.

17. The method of claim 1, wherein the mammal is a dysbiotic infant having a stool pH of 5.5 or above, 6.0 or above, or 6.5 or above.

18. The method of claim 1, wherein the bacterial composition is administered for a period and in an amount sufficient to maintain bacterial species capable of consuming MMO by internalization of that MMO within bacterial cell at a level of at least $10^6$ cfu/g feces, preferably $10^8$ cfu/g feces.

19. The method of claim 1, wherein the MMO is administered to said mammal prior to the administration of the bacterial composition, or wherein the MMO is administered to said mammal after the administration of the bacterial composition, or wherein the MMO is administered to said mammal contemporaneously with the administration of the bacterial composition.

* * * * *